United States Patent [19]

Morong, III et al.

[11] 4,042,465
[45] Aug. 16, 1977

[54] MEASUREMENT OF OXYGEN IN A FLUID SAMPLE AND APPARATUS THEREFOR

[75] Inventors: William H. Morong, III, Perry, Maine; Thomas E. Lawson, Denver, Colo.

[73] Assignee: Lexington Instrument Corporation, Waltham, Mass.

[21] Appl. No.: 717,645

[22] Filed: Aug. 25, 1976

[51] Int. Cl.² ............................................. G01N 27/46
[52] U.S. Cl. ................................ 204/1 T; 204/195 R; 324/29
[58] Field of Search .............. 324/29; 204/1 T, 195 R

[56] References Cited

U.S. PATENT DOCUMENTS

| 2,662,211 | 12/1953 | Marko et al. | 324/29 |
| 3,282,803 | 11/1966 | Poepel et al. | 204/1 T |
| 3,313,720 | 4/1967 | Robinson | 204/195 R |

Primary Examiner—G. L. Kaplan
Attorney, Agent, or Firm—Robert T. Dunn

[57] ABSTRACT

An electrical system for automatically measuring, computing and indicating the oxygen content in a sample of fluid, using a galvanic cell that absorbs and consumes the oxygen from the sample, produces controlled current pulses of given duration that are conducted by the cell as necessary to maintain the cell voltage constant and these pulses are counted during controlled intervals and the count is displayed as a representation of the oxygen content of the sample.

11 Claims, 5 Drawing Figures

MEASUREMENT OF OXYGEN IN A FLUID SAMPLE AND APPARATUS THEREFOR

BACKGROUND OF THE INVENTION

This invention relates to methods and apparatus for measuring the oxygen content of fluids and more particularly for measurement of oxygen in blood or respired gasses.

Heretofore, a galvanic cell with a resistive load has been employed to measure the oxygen content by percent of volume of respired air. One technique is to introduce a known amount of the respired air to an enclosed galvanic cell which is isolated from all other ambient fluids. The galvanic cell materials absorb the oxygen from the respired air and the electric current drawn by the cell consumes the absorbed oxygen and so is representative of the absorbed oxygen which, in turn, is representative of the oxygen content of the sample. A measure of the voltage across the load provides an indication of the oxygen of the sample. An exact measurement of the oxygen content of the sample is then calculated by reference to charts and/or tables. Since these calculations are time consuming, the exact measurement is not immediately obtained.

The exact measurement so determined should take into account that the electric current drawn by the galvanic cell even before the sample is introduced to the cell is at some low, yet significant level, depending upon the cell design, prior use and the ambient conditions at the time of the test. Since these factors vary from cell to cell and from time to time for a given cell, they introduce an uncertainty in the reading from the cell.

SUMMARY OF THE INVENTION

It is an object of the present invention to provide a method and electrical computer apparatus for use in conjunction with a galvanic cell to measure the oxygen content of a fluid sample by which some of the limitations of prior technique are avoided.

It is another object of the present invention to provide special computer apparatus for use with a galvanic cell for measuring the oxygen content of a fluid sample whereby uncertainties in measurements due to variations of the cell are substantially avoided.

It is another object to provide an electrical computer system that controls the current drawn by a galvanic cell used to measure the oxygen content of a fluid sample and immediately compute the oxygen content of the sample and present an indication of the same.

It is another object to provide a method of testing a fluid sample to determine the oxygen content of the sample using a galvanic cell by which at least some of the above mentioned limitations of prior techniques are avoided.

It is a further object to provide such a method and an electrical computer for carrying out the method which produces a more reliable measure of the oxygen content of the sample than can be provided by the techniques of prior methods and apparatus.

Another purpose is to provide a method and apparatus for measuring, computing and indicating the total volume percent of oxygen in a sample of blood.

It is another purpose to provide a method and apparatus for measuring, computing and indicating the total volume percent of oxygen in a sample of respiration.

In accordance with one feature of the present invention, a sample of blood or respiration is introduced into a container and an oxygen-free neutral gas is also introduced into the container, mixed with the sample and then removed from the container and introduced into the galvanic cell, whereupon the cell absorbs the oxygen carried to it by the neutral fluid and is not contaminated by other materials in the sample.

The technique of the present invention is to maintain the voltage across the galvanic cell at a substantially constant zero level by feeding controlled current pulses of predetermined duration to the cell as necessary to maintain the voltage across the cell at zero. This prevents a potential accumulation across the cell anode and cathode that causes electrolysis, that, in turn, causes larger cell response time and decreases the accuracy of the cell.

The current pulses each carry the same predetermined amount of electric charge (coulombs) to the cell and account for the same amount of absorbed oxygen; and so a count of the number of these pulses required to neutralize the cell voltage produced by absorbed oxygen represents the amount of absorbed oxygen. In a preferred embodiment there are two operating modes, the "standby" mode" and the "measure mode" operated in sequence. During both modes, the neutral fluid flows through the cell. Before the sample containing oxygen is introduced into nuetral fluid, a first, or standby count number is produced and stored providing a background count. Then, upon introducing the sample into the neutral fluid, a second count, the measure count, is commenced and, to the extent that the second count exceeds the first count, representative pulses are produced which are counted to indicate the oxygen content of the sample.

The output indication during the first count (the standby mode of operation) is isolated, and then controls the output indication during the second count, (the measure mode of operation), in case the background level of oxygen in the galvanic cell exceeds a preset limit due to incomplete consumption of the last traces of oxygen from a previous test. Thereafter, a strobe of the output is initiated at regular intervals until the undesireable condition passes.

These and other objects and features of the present invention will be apparent to those skilled in the art in view of the specific descriptions of embodiments of the invention contained herein taken in conjunction with the drawings.

DESCRIPTION OF EMBODIMENTS OF THE INVENTION

Measurement of the oxygen content of any body liquid and measurement of the oxygen content of any respiration is made by taking a sample of the liquid or a sample of the respiration. The sample is a given known volume, usually at atmospheric pressure. For example, by maintaining uniform conditions during the measurement of a sample of blood, absolute oxygen content of the blood sample can be obtained. It is generally desired that the samples be as small as possible and that the measurement be made as quickly as possible. For example, to measure Cardiac Output by the Fick Method, three samples are tested in sequence, a sample of expired air, a sample of arterial blood and a sample of mixed venous blood. A single machine that measures each of these samples in rapid sequence is desireable.

Figure 1:
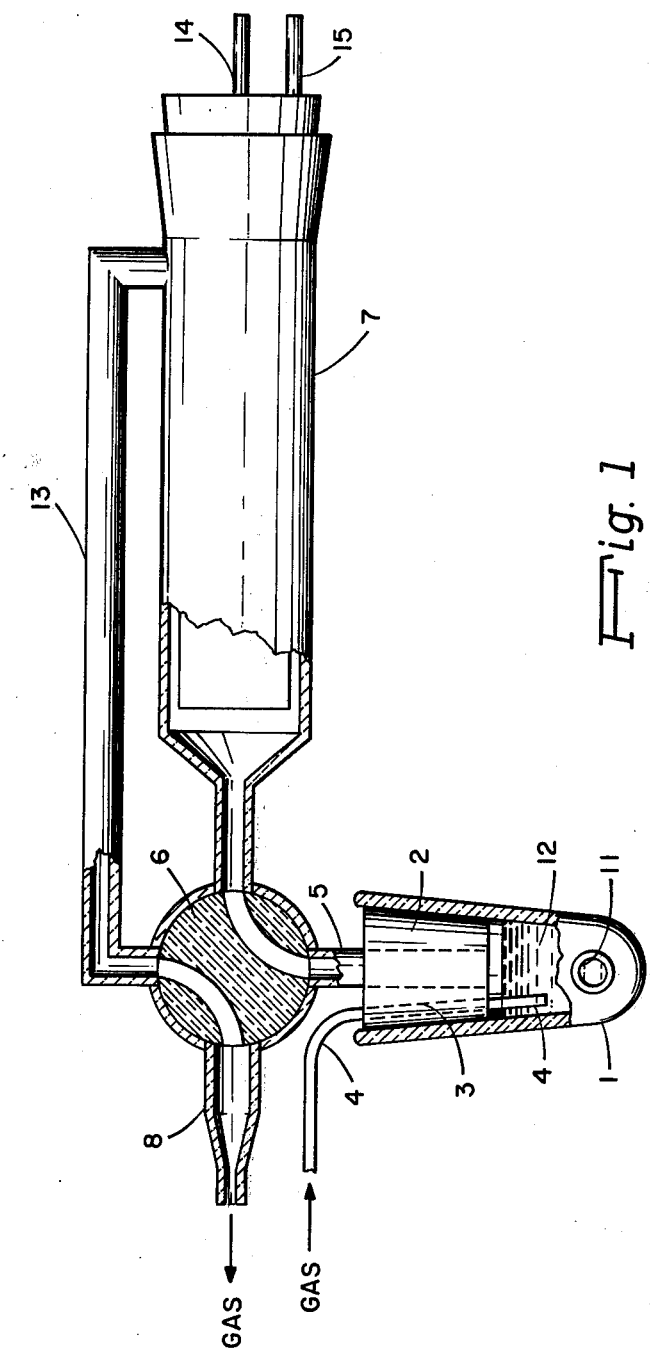
FIG. 1 is a partially cross-sectioned view of mechanical apparatus of the present invention including the galvanic cell.

In accordance with one feature of the present invention, oxygen is extracted from the sample using a neutral fluid. The neutral fluid absorbs the oxygen and carries the oxygen to the galvanic cell. The cell absorbs the oxygen from the neutral fluid and generates a current output at the cell terminals. FIG. 1 shows mechanical apparatus for doing this.

Turning to FIG. 1 there is shown in cross-section a scrubber chamber 1 plugged by a glass plug 2 through which there are two passages; passage 3 into which a metal tube 4 is inserted for carrying an inert gas into the scrubber chamber; and passage 5 which leads to a stop-cock valve 6 that feeds the flow from the chamber either into the galvanic cell 7 or bypasses the cell and vents the flow of gas to the atmosphere through outlet 8.

Another passage into the scrubber chamber, called the injection port 11 accommodates insertion of the sample fluid through a rubber seal into the chamber. The sample is preferably inserted into the chamber and mixes with distilled water 12 in the chamber. The metal tube carrying the gas input into the chamber extends into the distilled water so that injected inert gas bubbles throughout the water and absorbs the oxygen from the sample.

The standby mode of operation is accomplished before the sample is inserted into the scrubber chamber. During this mode, the stop-cock is in the USE position shown in FIG. 1 and gas is bubbled into the distilled water and flows through the stop-cock into one end of the galvanic cell 7 and flows from the other end of the galvanic cell through tube 13 back to the stop-cock from where it is routed to the atmosphere. The electrical computer circuits coupled to the two electrodes 14 and 15 of the galvanic cell detect the cell voltage and feed measured current pulses to the cell as necessary to maintain the cell voltage at zero and so a count of these pulses during the standby mode is an indication of the background signal level of the system. Then, the sample is injected into the scrubber chamber and, simultaneously, the measure mode of operation begins.

Figure 2:
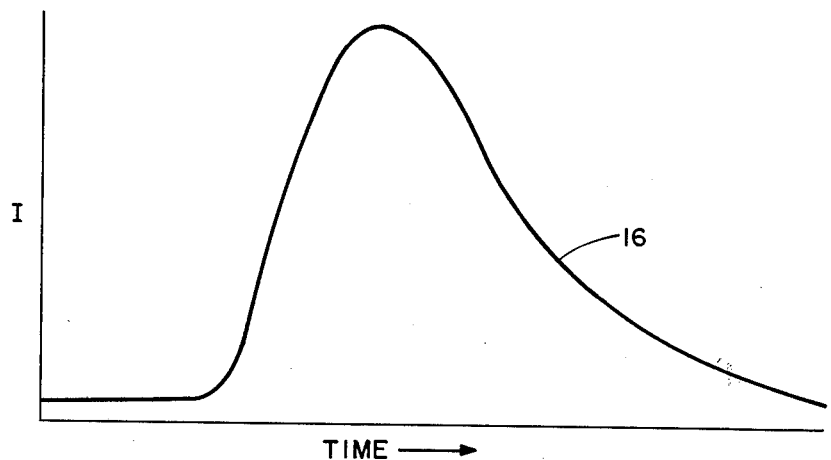
FIG. 2 is a representative curve of galvanic cell current verses time following introduction of oxgyen from a sample to the cell for constant voltage operation.

If the measure mode of operation commences with the stop-cock in the position shown in FIG. 1 and immediately upon starting, the sample is injected into the scrubber chamber, the current flow through the galvanic cell commences from a very low value, just before oxygen is carried by the gas up to the cell. Then, as oxygen is absorbed by the cell, the current to the cell increases sharply. If the voltage across the galvanic cell is maintained constant, the current will reach a peak at the point of maximum oxygen absorption and then taper off as the absorbed oxygen is consumed and is not replaced as the sample is depleted. A plot or curve of this current versus time for the constant voltage operation is essentially as illustrated in FIG. 2 and represented by curve 16.

In accordance with a preferred feature of the present invention, rather than using a resistive load for the galvanic cell during a test, the cell voltage is held at zero volts with a null type control system by pulsing the cell with current pulses as necessary to hold the cell voltage at zero volts. During the measurement, the current flow through the galvanic cell varies in proportion to the oxygen consumed by the cell and the total current charge is a measure of the total amount of oxygen consumed. This total current charge is represented by the total number of current pulses of fixed predetermined mangitude and duration that are fed to the cell during the test. By this technique, it is then only necessary to count the number of current pulses required to use up the oxygen absorbed by the galvanic cell to get a measure of the amount of the absorbed oxygen and, hence, a measure of the oxygen content of the sample.

Figure 3:
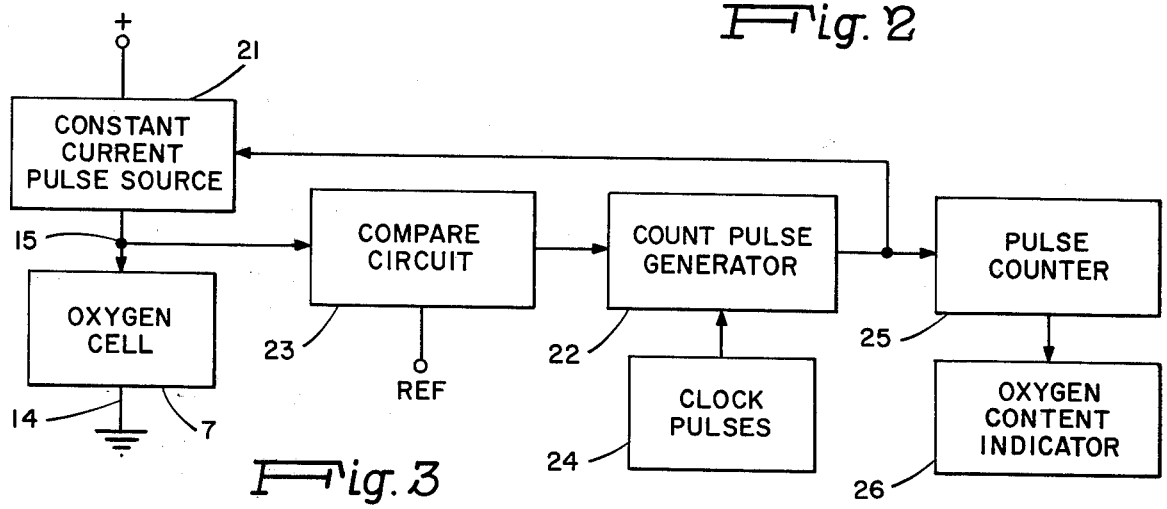
FIG. 3 is a general, functional block diagram showing the functions of electrical circuits incorporating features of the present invention for carrying out the measure mode of operation to detect and indicate the oxygen content of the sample.

The essential functions of the present invention, performed by a special digital computer, are illustrated in FIG. 3. The galvanic cell 7 has two terminals 14 and 15. Terminal 14 is grounded and constant current pulses are applied to terminal 13 from the constant current source 21, controlled by pulses from the counter pulse generator 22. The voltage at terminal 15 is compared with the ground voltage by compare circuit 23 and when the cell voltage exceeds the ground voltage, clock pulses derived from 24 are fed by the count pulse generator to the constant current source so that each clock pulse applied to the constant current source releases a pulse of current from the source to the cell. A count of the clock pulses that initiate constant current pulses to the cell by counter 25 is indicated at 26 as a representation of oxygen content of the sample under test.

It is usual that a galvanic cell exhibits a background current before it is charged with oxygen and a slight background current is required to counteract the background current. This background current will vary from time to time for a given cell and will vary from cell to cell. The presence of the background current requirement of the cell introduces an uncertainty or slight error in the measurement of oxygen content using the system described functionally in FIG. 3. This uncertainty can be substantially reduced and even eliminated using the system described functionally in FIG. 4. This system includes all of the same functional parts as the system in FIG. 3 and those parts bear the same reference numbers. In addition, the background current is represented by a stored count of pulses stored in a shift register 27 obtained during the standby mode of operation. During the standby mode of operation, before the galvanic cell is charged with oxygen, the pulse rate is low. For example, every few seconds a pulse derived from the clock 24 is applied to the constant current source, even while the clock 24 is producing pulses at a relatively high rate. The clock pulses that initiate constant current pulses to the cell during the standby mode are loaded into the shift register 27 at a slow-down rate. The slow-down rate is accomplished by a clock pulse countdown that advances the shift register and synchronizes the feed of background pulses into the shift register. Thus, over a predetermined interval determined by the clock pulse rate and the countdown, the background current pulses fed to the cell are stored in the shift register. During this mode of operation, the count and indication by 25 and 26 are disabled.

Just before the cell is charged with oxygen, the measure mode of operation starts by closing a switch 31 to initiate recirculation of the background current pulses stored in the shift register. Constant current pulses are then applied to the cell to maintain the charged cell voltage at zero. Clearly, the rate of these constant current pulses required for the charged cell is much greater than the background rate. From these pulses are subtracted, by 32, the background pulses stored in the shift register. More particularly, during each unit of time that the measurement is made, the background pulses stored in the shift register are recirculated continually and as each background pulse appears in the recirculation it subtracts or eliminates one of the pulses to be counted by 25 as a count of the constant current pulses fed to the charged cell. Thus, the measurement of oxygen content of a sample is made in two steps, the standby mode and the measure mode and all the functions performed by the system are readily carried out by common binary circuits. Furthermore, these two rates, the background rate and the charged cell rate and the subtraction of one from the other are all achieved using but a single shift register and the subtract function 32 can be accomplished, as is apparent to those skilled in the art, using but a simple NAND circuit and does not require registers. A suggested combination and arrangement of well known and available binary logic circuits to accomplish the functions illustrated in FIG. 4, as well as those illustrated in FIG. 3, is shown in FIG. 5.

Figure 4:
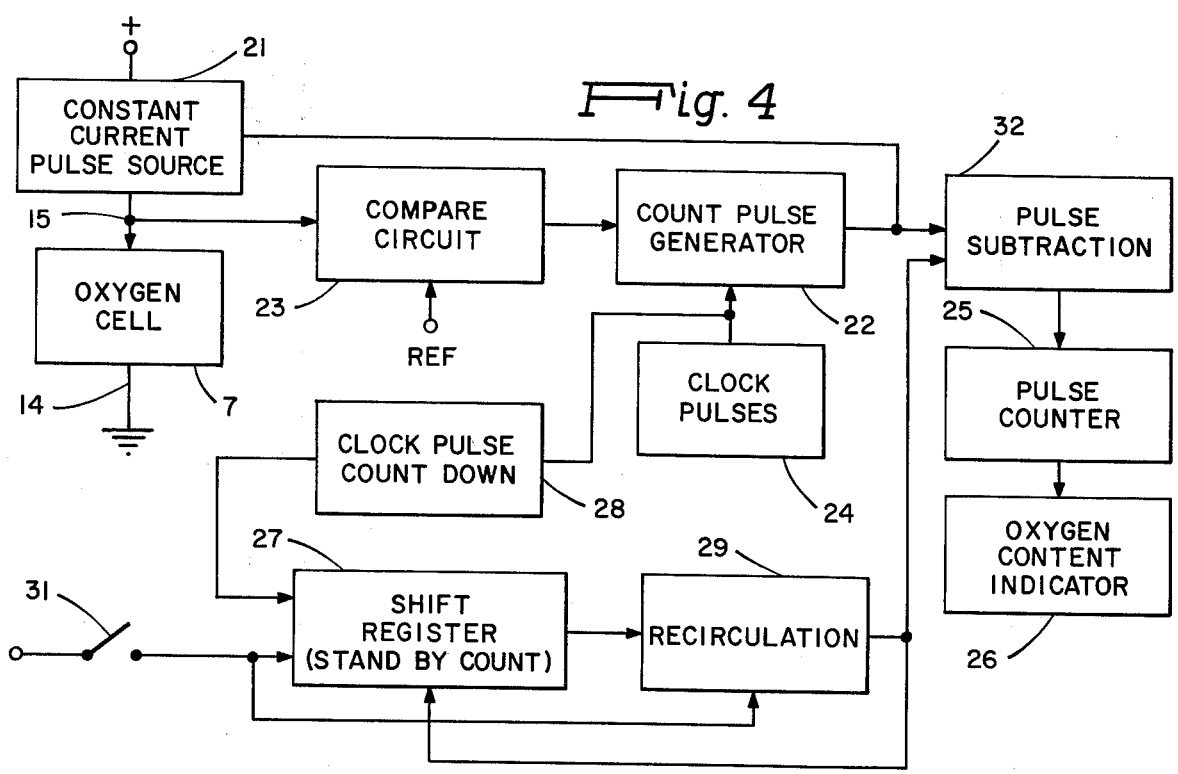
FIG. 4 is another functional block diagram illustrating operation to carry out both the standby and the measure modes of operation.
Figure 5:
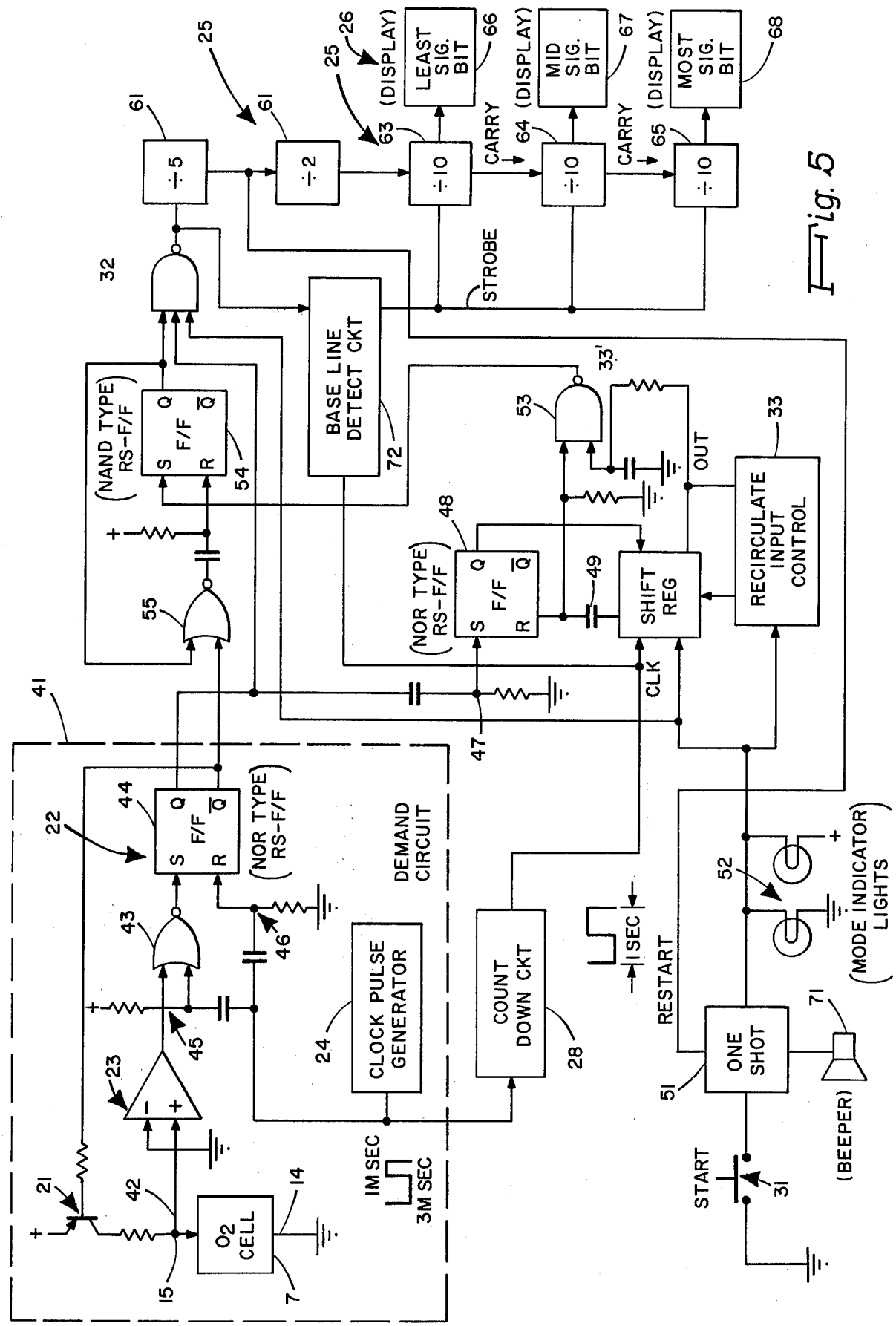
FIG. 5 is a block diagram showing substantially conventional circuit elements of an embodiment of the present invention and controls for operation in the standby and measure modes and which terminates the measure mode when background level of oxygen in the galvanic cell falls to the original background level.

The parts and circuits shown in FIG. 5 which perform the same function as blocks in FIGS. 3 and 4 bear the same reference numbers where practicable. This is done as an aid to understanding the functioning of the circuits in FIG. 5. The demand circuit 41 in FIG. 5 includes all of the controls of current pulses to galvanic cell 7. As the cell consumes oxygen, it draws the non-inverting input 42 of the comparator circuit 23 below ground potential, forcing the comparator circuit output to go negative. Meanwhile, the clock pulse generator 24 produces a 1 millisecond clock pulse every 4 milliseconds. Once the comparator output goes negative, at the next negative going clock pulse transition, the output of NOR gate 43 goes positive setting flip-flop (F—F) 44 and initiating a pulse of feed back current (a constant current pulse) to return the cell to a slightly positive potential. In other words, each time F—F 44 is switched from reset to set the base of the constant current control transistor 21 goes negative and a current pulse to the cell is initiated. That current pulse to the cell is terminated when F—F 44 is reset by the next positive going clock pulse edge. The leading edges of the clock pulses are fed to NOR circuit 43 and to the reset input of F—F circuit 44 by differentiator circuits 45 and 46, respectively. Hence, the demand circuit 41 includes a null-type feed back loop that, throughout the test, pulses the cell as necessary to maintain the cell at a slightly positive potential with respect to the reference ground.

In the standby mode of operation when background current to the cell is measured, the current pulse rate to the cell is very slow and may be on the order of five to 20 pulses per minute. This frequency indicates the background level of oxygen entering the cell. And is stored in the shift register 27 to be subtracted from the pulse train during the measure cycle when the cell is charged with oxygen from the sample. In the standby mode, the shift register 27 is held in the non-recirculating condition. Each positive going pulse from the Q output of F—F circuit 44, produced by differentiator circuit 47, sets F—F circuit 48 which loads a ONE bit into the shift register at the next slow clock pulse. The slow clock pulses are obtained from clock pulse count down circuit 28 which, for example, counts down 128 and so produces a slow clock pulse each second. Then F—F circuit 48 is reset by the same slow clock pulse, slightly delayed and obtained from the shift register. For this purpose a delay circuit 49 is provided from the shift register to F—F circuit 48.

The timing sequence of the system during the standby mode of operation may be as follows. The clock pulse rate is 128 pulses per second, and is divided by 128 by the count down circuit 28 producing the slow clock pulses at the rate of two per second. During the Standby mode of operation the slow clock pulses step the shift register through at least one complete cycle. If this register is a 64 bit register, then it is stepped through a full cycle of 32 seconds and during those 32 seconds, the background current pulses fed to the cell are stored in the shift register. When that storage is completed the system is ready for the measure mode of operation.

The measure mode of operation is initiated by pressing the start button 31 just before the cell is charged with oxygen from the test sample. The start switch 31 grounds an input to one shot multivibrator 51, the output of which controls the recirculation output 83 of the shift register 27. Also, one of the mode indicator lights 52 labeled "Measure" is illuminated. Now, each time a ONE bit appears at the shift register recirculating output 33, and it is synchronized with the delayed clock pulse from 49, a negative going pulse appears in the output of NAND gate circuit 53. The negative going output from 53 sets F—F circuit 54 making its Q output go down which prevents a positive at the output of NAND gate circuit 32. The first time a pulse is blocked in this way by gate circuit 32, a pulse is produced by NOR circuit 55 which resets F—F circuit 54. Thus, the recirculating output of the shift register, recirculating once each 32 seconds, is subtracted from the count of constant current pulses fed to the charged cell during the measure mode of operation and so the pulses appearing at the output of NAND gate 32 includes all of the pulses that initiate a charge of current to the cell, minus the background pulses stored in the shift register with each circulation of the shift register. In other words, during a unit interval of time determined by the clock pulse rate, the clock pulse countdown and the stages of the shift register, the background count is subtracted from the measure count yielding a net count of pulses per unit time and the total count of the net count is representative of the total amount of oxygen charged into the cell.

The output of NAND gate 32 is divided by 10 by divide circuit 61 and accumulated in a three digit decimal counter display 25-26 which includes, for example, three divide by 10 circuits 63, 64 and 65 and three display circuits 66, 67 and 68 that display the least, the intermediate and the most significant bits of a decimal number.

The end of the measure mode of operation occurs when the rate of pulses from NAND gate 32 falls below a predetermined number. For example, when five pulses do not occur in 20 seconds the measure mode of operation may be terminated and a tone sounded. For this purpose a signal representing every five pulses that passes through NAND gate 32 and obtained at the output of divider 61, may be applied to one shot multivibrator 51 to initiate a tone from speaker 71.

If it should occur that the background level of oxygen in the cell becomes higher than the preset limit, as can occur when there is incomplete consumption of oxygen in a previous test, a baseline detector circuit 72 strobes display 26 after completion of the measure mode causing the display to blink until the condition passes. Clearly, when the condition passes the display remains steady and the operator then knows that the condition has passed. Base line detector 72 may, for example, function to integrate pulses from NAND gate 32 over a preset time interval and compare the resulting level with a preset level and when it exceeds the preset level the display is strobed.

The method and apparatus of the present invention represented by embodiments illustrated by FIGS. 3 and 4 and described in greater detail herein with reference to FIG. 5 all include a demand function by which constant current pulses are fed to the galvanic cell that has absorbed oxygen from the test sample, as necessary to maintain the voltage across the cell at the substantially zero value so that a count of the current pulses is representative of the amount of oxygen abosrbed and consumed by the cell. These features and other features illustrated in the embodiments described herein may be implemented by other structures than those specifically described herein as will be apparent to those skilled in the art, without deviating from the spirit and scope of the invention as set forth more fully in the claims.

What is claimed is:

1. In apparatus for measuring the oxygen content of a fluid sample including a galvanic cell that absorbs the oxygen from the sample, means for measuring the oxygen absorbed by the cell comprising,
    a. electrical means connected to the cell for detecting the voltage across the cell, herein called the cell voltage, and for controlling electric current to the cell, herein called the cell current, so that the cell voltage does not exceed a standard voltage,
    b. means for integrating the values of the cell currents, and
    c. means for indicating the value of said integration as representative of the oxygen absorbed by the cell.

2. Apparatus as in claim 1 wherein said means for controlling cell current and said integrating means include:
    a. a clock pulse generator,
    b. a source of cell reference voltage,
    c. a source of cell energization voltage,
    d. means for comparing the cell voltage and the cell reference voltage producing a feedback signal
    e. means responsive to the feedback signal and the clock pulses for producing cell current count pulses of uniform duration,
    f. a controlled switch coupling the cell energization voltage to the cell, and
    g. means for coupling the current count pulses to the controlled switch for controlling the switch,
    h. whereby each count pulse closes the controlled switch during the uniform duration, and
    i. means for counting said count pulses,
    j. whereby said count of count pulses is a measure of the integrated cell current.

3. Apparatus as in claim 1 wherein said means for controlling cell current and said integrating means include:
    a. a clock pulse generator,
    b. a source of cell reference voltage,
    c. a source of cell energization voltage,
    d. a two input bi-stable flip-flop circuit,
    e. means for coupling the clock pulses to one of the said flip-flop circuits inputs,
    f. a NOR circuit responsive to the clock pulses and the feedback signal,
    g. the other input of the flip-flop circuit being responsive to the output of the NOR circuit,
    h. a transistor switch electrically between the source of energization voltage and the cell, and
    i. means for coupling one output of the flip-flop circuit to the switch, thereby controlling the switch,
    j. whereby each count pulse closes the switch during the uniform interval, and
    k. means for counting said count pulses,
    l. whereby said count of count pulses is a measure of the integrated cell current.

4. Apparatus as in claim 3 wherein,
    a. the means for comparing is an operational amplifier.

5. Apparatus as in claim 4 wherein,
    a. the cell reference voltage is ground potential.

6. Apparatus as in claim 3 wherein,
    a. the clock pulses are coupled to a differentiating circuit before coupling to the flip-flop circuit input and before coupling to the NOR circuit input,
    b. whereby the uniform duration is the intervals between clock pulses.

7. Apparatus as in claim 3 wherein,
    a. the flip-flop circuit has a set, S, and a reset, R, input and corresponding Q and $\overline{Q}$ outputs,
    b. the NOR circuit output is coupled to the S input,
    c. the clock pulses are coupled to the R input, and
    d. the Q output is coupled to the transistor switch for controlling the switch.

8. Apparatus as in claim 3 and further including,
    a. a shift register,
    b. means for feeding count pulses to the shift register for storage therein during a predetermined interval of time before the cell absorbs oxygen from the sample,
    c. means for recirculating the pulses stored in the shift register following absorption of oxygen by the cell, and
    d. means responsive to the recirculated stored pulses and the count pulses produced following absorption of oxygen by the cell for inhibiting one count pulse for each recirculated stored pulse,
    e. whereby the count of the remainder of said count pulses is representative of the oxygen from the sample that is absorbed by the cell.

9. Apparatus as in claim 8 wherein said recirculation of pulses is cycled repeatedly and the remainder of the count pulses are counted until the rate of the remainder of the count pulses is less than a predetermined rate.

10. Apparatus as in claim 1 and further including,
    a. means for storing the integral of cell current before the cell absorbs oxygen, and
    b. means for reducing the integral of cell current following absorption of oxygen by the cell by the amount of the stored integral, c. whereby the reduced integral of cell current following absorption of oxygen by the cell is representative of the oxygen absorbed by the cell.

11. In a method of measuring the oxygen content of a fluid sample using a galvanic cell that absorbs the oxygen from the sample, the steps of:
   a. generating clock pulses of uniform interval between pulses;
   b. providing a controlled source of constant current for the cell;
   c. comparing cell voltage with a reference voltage producing a feedback signal when cell voltage exceeds the reference voltage;
   d. combining clock pulses with the feedback signal producing cell current count pulses of uniform duration;
   e. applying the cell current count pulses to the controlled source of constant current; whereby a pulse of constant current for the uniform duration is conducted by the cell for each applied cell current count pulse; and
   f. counting the cell current count pulses.

* * * * *